US 007858854B2

(12) United States Patent
Martinelli et al.

(10) Patent No.: US 7,858,854 B2
(45) Date of Patent: Dec. 28, 2010

(54) PLANTS AND SEED OF INBRED CORN VARIETY DS-046358

(75) Inventors: Dan Martinelli, Janesville, WI (US); Ryan Mueller, Beloit, WI (US); Gary Day, Beloit, WI (US); Paul Sun, Roscoe, IL (US)

(73) Assignee: Dairyland Seed Co., Inc., West Bend, WI (US)

( * ) Notice: Subject to any disclaimer, the term of this patent is extended or adjusted under 35 U.S.C. 154(b) by 248 days.

(21) Appl. No.: 12/035,050

(22) Filed: Feb. 21, 2008

(65) Prior Publication Data

US 2009/0217408 A1 Aug. 27, 2009

(51) Int. Cl.
*A01H 1/00* (2006.01)
*C07H 21/04* (2006.01)
*C07K 14/415* (2006.01)
*C12N 15/00* (2006.01)

(52) U.S. Cl. .................... 800/320.1; 435/468; 435/412; 435/418; 435/424; 530/370; 536/23.1; 800/260; 800/278; 800/303

(58) Field of Classification Search .................. 435/6, 435/69.1, 468, 183, 419, 320.1; 536/23.2, 536/23.6; 800/278, 295, 320.1
See application file for complete search history.

(56) References Cited

U.S. PATENT DOCUMENTS 5,523,520 A   6/1996   Hunsperger et al.
6,025,547 A   2/2000   Stucker
6,096,953 A   8/2000   Hoffbeck
6,459,022 B1  10/2002  Day
7,301,082 B2  11/2007  Kilgore-Norquest
7,629,511 B1 * 12/2009  Piper .................... 800/320.1

OTHER PUBLICATIONS

Allard, R.W. in Principles of Plant Breeding, John Wiley & Sons, Inc. (1960) 155-156.
Eshed, Y. et al., "Less-than-additive epistatic interactions of quantitative trait loci in tomato," Genetics (1996) 1807-1817.
Kraft, T. et al., "Linkage disequilibrium and fingerprinting in sugar beet," Theor. Appl. Genet. (2000) 101:323-326.
Murray, M.G. et al., "Restriction fragment length polymorphisms: What are they and how can breeders use them?" Proceedings of the 43rd Annual Corn and Sorghum Research Conference (1988) 43:72-87.
Phillips, R.L. et al., "Cell/tissue culture and in vitro manipulation," Corn & Corn Improvement-Argonomy Monograph No. 18, 3rd Edition, Chapter 5, (1988) pp. 345 and 358-359.

* cited by examiner

*Primary Examiner*—Phuong T Bui
(74) *Attorney, Agent, or Firm*—Michael Best & Friedrich LLP

(57) ABSTRACT

Disclosed is the seed of an inbred corn line, designated DS-046358, a sample of which is deposited under ATCC Accession No. PTA-9052. Also disclosed are plants, or parts thereof, grown from the seed of the cultivar, plants having the morphological and physiological characteristics of inbred corn line DS-046358, and methods of using the plant or parts thereof in a corn breeding program.

25 Claims, No Drawings

PLANTS AND SEED OF INBRED CORN VARIETY DS-046358

CROSS REFERENCE TO RELATED APPLICATIONS

Not applicable.

STATEMENT REGARDING FEDERALLY SPONSORED RESEARCH OR DEVELOPMENT

Not applicable.

INTRODUCTION

The present invention relates to inbred corn seed and plants of the variety designated DS-046358, and derivatives and tissue cultures thereof.

The goal of field crop breeding is to combine various desirable traits in a single variety/hybrid. Such desirable traits include improved yields, stalks, and roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Corn (*Zea mays* L.) plants have separate male and female flowers on the same plant, located on the tassel and the ear, respectively and can be bred by both self-pollination and cross-pollination. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. The development of uniform corn plant hybrids requires the development of homozygous inbred plants, the crossing of these inbred plants, and the evaluation of the crosses.

A single cross hybrid corn variety is the cross of two inbred plants, each of which has a genotype which complements the genotype of the other. The hybrid progeny of the first generation is designated $F_1$. Typically, $F_1$ hybrids are more vigorous than their inbred parents. This hybrid vigor, or heterosis, is manifested in many polygenic traits, including markedly improved yields, better stalks, better roots, and better insect and disease resistance. In the development of hybrids only the $F_1$ hybrid plants are typically sought.

North American farmers alone plant tens of millions of acres of corn annually. There are extensive commercial corn breeding programs worldwide. A continuing goal of these programs is to develop corn hybrids having one or more desirable characteristics by crossing stable inbred plants. Thus, there is a need in the art for inbred parental plants having desirable characteristics.

SUMMARY OF THE INVENTION

In one aspect, the present invention provides seed of corn inbred line designated DS-046358, representative seed of the line having been deposited under ATCC Accession No. PTA-9052 on Mar. 13, 2008, plants, or parts thereof, grown from the seed. Also provided is a tissue culture of regenerable cells from the plant, or part thereof.

In another aspect, the invention provides a plant, or a part thereof, having all the physiological and morphological characteristics of DS-046358, representative seed of the line having been deposited under ATCC Accession No. PTA-9052 on Mar. 13, 2008.

The invention also provides a method for producing corn seed, comprising crossing a first parent corn plant with a second parent corn plant, at least one of the first and second parent corn plants being of the inbred line designated DS-046358, representative seed of the line having been deposited under ATCC Accession No. PTA-9052 to yield corn seed, and hybrid seed produced by the method, hybrid corn plants grown from the seed.

In yet another aspect is provided a method of producing an inbred corn plant derived from the inbred corn line designated DS-046358 by crossing a progeny plant derived from the inbred corn line designated DS-046358 with a second corn plant to produce a seed of a progeny plant of a subsequent generation. A progeny plant of a subsequent generation is produced from the seed and crossed with itself or a second plant. These crossings are repeated for an additional three to ten generations to produce an inbred corn plant derived from the inbred corn line designated DS-046358.

DETAILED DESCRIPTION OF THE INVENTION

I. Definitions of Plant Characteristics

Anthracnose Stalk Rot (*Colletotrichum graminicola*): A 1 to 9 visual rating indicating the resistance to Anthracnose Stalk Rot. A higher score indicates a higher resistance.

Artificial Brittle Stalk: A count of the number of "snapped" plants per plot following machine snapping. A snapped plant has its stalk completely snapped at a node between the base of the plant and the node above the ear. Expressed as percent of plants that did not snap.

Barren Plants: Plants that are barren, i.e., lack an ear with grain, or have an ear with only a few scattered kernels.

Brittle Stalks: This is a measure of the stalk breakage near the time of pollination, and is an indication of whether a hybrid or inbred would snap or break near the time of flowering under severe winds. Data are presented as percentage of plants that did not snap.

Cg: *Colletotrichum graminicola* rating. Rating times 10 is approximately equal to percent total plant infection.

CLN: Corn Lethal Necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Common Rust (*Puccinia sorghi*). A 1 to 9 visual rating indicating the resistance to Common Rust. A higher score indicates a higher resistance.

Cross pollination. A plant is cross pollinated if the pollen comes from a flower on a different plant from a different family or line. Cross pollination excludes sib and self pollination.

Cz: *Cercospora zeae-maydis* rating. Rating times 10 is approximately equal to percent total plant infection.

Dgg: *Diatraea grandiosella* girdling rating (values are percent plants girdled and stalk lodged).

*Diplodia* Ear Mold Scores (*Diplodia maydis* and *Diplodia macrospora*). A 1 to 9 visual rating indicating the resistance to *Diplodia* Ear Mold. A higher score indicates a higher resistance.

*Diplodia* Stalk Rot Score. Score of stalk rot severity due to *Diplodia* (*Diplodia maydis*). Expressed as a 1 to 9 score with 9 being highly resistant.

Dropped Ears: Ears that have fallen from the plant to the ground.

Drought Tolerance. This represents a 1 to 9 rating for drought tolerance, and is based on data obtained under stress conditions. A high score indicates good drought tolerance and a low score indicates poor drought tolerance.

Drydown: This represents the relative rate at which a hybrid will reach acceptable harvest moisture compared to other hybrids on a 1 to 9 rating scale. A high score indicates a hybrid that dries relatively fast while a low score indicates a hybrid that dries slowly.

Dsp: *Diabrotica* species root ratings (1=least affected to 9=severe pruning).

Ear Height. The ear height is a measure from the ground to the highest placed developed ear node attachment and is measured in centimeters.

Ear Texture. A 1 to 9 visual rating was used to indicate the relative hardness (smoothness of crown) of mature grain. A 1 would be very soft (extreme dent) while a 9 would be very hard (flinty or very smooth crown).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Early Brittle Stalk. A count of the number of "snapped" plants per plot following severe winds when the corn plant is experiencing very rapid vegetative growth in the V5-V8 stage. Expressed as percent of plants that did not snap.

Early Growth. This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute higher score.

Early Root Lodging Score. Score for severity of plants that lean from a vertical axis at an approximate 30 degree angle or greater which typically results from strong winds prior to or around flowering recorded within 2 weeks of a wind event. Expressed as a 1 to 9 score with 9 being no lodging.

Early Root Lodging. The percentage of plants that do not root lodge prior to or around anthesis; plants that lean from the vertical axis at an approximately 30 degree angle or greater would be counted as root lodged.

Early Stand: The percent of plants that emerge from the ground as determined in the early spring.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

ER: Ear rot rating (values approximate percent ear rotted).

European Core Borer Dropped Ears (*Ostrinia nubilalis*). Dropped ears due to European Corn Borer. Percentage of plants that did not drop ears under second generation European Corn Borer infestation.

European Core Borer First Generation Leaf Feeding (*Ostrinia nubilalis*). A 1 to 9 visual rating indicating the resistance to preflowering leaf feeding by first generation European Corn Borer. A higher score indicates a higher resistance.

European Core Borer Second Generation (*Ostrinia nubilalis*). A 1 to 9 visual rating indicating post flowering degree of stalk breakage and other evidence of feeding by second generation European Corn Borer. A higher score indicates a higher resistance.

European Core Borer Second Generation Inches of Tunneling (*Ostrinia nubilalis*). Average inches of tunneling per plant in the stalk.

Eye Spot (*Kabatiella zeae* or *Aureobasidium zeae*). A 1 to 9 visual rating indicating the resistance to Eye Spot. A higher score indicates a higher resistance.

Final Stand Count: The number of plants just prior to harvest.

*Fusarium* Ear Rot Score (*Fusarium moniliforme* or *Fusarium subglutinans*). A 1 to 9 visual rating indicating the resistance to *Fusarium* Ear Rot. A higher score indicates a higher resistance.

$$GDU=(\text{Max. temp.}+\text{Min. temp.})-50$$

GDUs To Shed. The number of growing degree units (GDUS) or heat units required for an inbred line or hybrid to have approximately 50 percent of the plants shedding pollen and is measured from the time of planting. Growing degree units are calculated by the Barger Method, where the heat units for a 24-hour period are:

GDUs to Shed: The number of growing degree units (GDUs) or heat units required for an inbred line or hybrid to have approximately 50% of the plants shedding pollen as measured from time of planting. GDUs to shed is determined by summing the individual GDU daily values from planting date to the date of 50% pollen shed.

GDUs to Silk: The number of growing degree units for an inbred line or hybrid to have approximately 50% of the plants with silk emergence as measured from time of planting. GDUs to silk is determined by summing the individual GDU daily values from planting date to the date of 50% silking.

GDUs: Growing degree units which are calculated by the Barger Method, where the heat units for a 24-h period are calculated as GDUs=[(Maximum daily temperature+Minimum daily temperature)/2]−50. The highest maximum daily temperature used is 86.degree. F. and the lowest minimum temperature used is 50.degree. F.

General Ear Mold. Visual rating (1 to 9 score) where a 1 is very susceptible and a 9 is very resistant. This is based on overall rating for ear mold of mature ears without determining the specific mold organism, and may not be predictive for a specific ear mold.

*Gibberella* Ear Rot (Pink Mold) (*Gibberella zeae*). A 1 to 9 visual rating indicating the resistance to *Gibberella* Ear Rot. A higher score indicates a higher resistance.

*Gibberella* Stalk Rot Score. Score of stalk rot severity due to *Gibberella* (*Gibberella zeae*). Expressed as a 1 to 9 score with 9 being highly resistant.

Goss' Wilt (*Corynebacterium nebraskense*). A 1 to 9 visual rating indicating the resistance to Goss' Wilt. A higher score indicates a higher resistance.

Grain oil. Absolute value of oil content of the kernel as predicted by Near-infrared Transmittance and expressed as a percent of dry matter.

Grain protein. Absolute value of protein content of the kernel as predicted by Near-infrared Transmittance and expressed as a percent of dry matter.

Grain Starch. Absolute value of starch content of the kernel as predicted by Near-infrared Transmittance and expressed as a percent of dry matter.

Gray Leaf Spot (*Cercospora zeae-maydis*). A 1 to 9 visual rating indicating the resistance to Gray Leaf Spot. A higher score indicates a higher resistance.

Growing Degree Units (GDUs). Using the Barger Heat Unit Theory, which assumes that maize growth occurs in the temperature range 50° F. to 86° F. and that temperatures outside this range slow down growth; the maximum daily heat unit accumulation is 36 and the minimum daily heat unit accumulation is 0. The seasonal accumulation of GDU is a major factor in determining maturity zones.

Harvest Moisture: The moisture is the actual percentage moisture of the grain at harvest.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Head Smut (*Sphacelotheca reiliana*). This score indicates the percentage of plants not infected.

*Helminthosporium Carbonium* Leaf Blight (*Helminthosporium carbonum*). A 1 to 9 visual rating indicating the resistance to *Helminthosporium* infection. A higher score indicates a higher resistance.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. +=indicates the presence of Ht chlorotic-lesion type resistance; −=indicates absence of Ht chlorotic-lesion type resistance, and +/−=indicates segregation of Ht chlorotic-lesion type resistance. Rating times 10 is approximately equal to percent total plant infection.

Inbred. A line developed through inbreeding or doubled haploidy that preferably comprises homozygous alleles at about 95% or more of its loci.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Late Root Lodging Score. Score for severity of plants that lean from a vertical axis at an approximate 30 degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with being no lodging.

Late Root Lodging. The percentage of plants that do not root lodge after anthesis through harvest; plants that lean from the vertical axis at an approximately 30 degree angle or greater would be counted as root lodged.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Maize Dwarf Mosaic Complex (Maize Dwarf Mosaic Virus and Maize Chlorotic Dwarf Virus). A 1 to 9 visual rating indicating the resistance to Maize Dwarf Mosaic Complex. A higher score indicates a higher resistance.

Northern Leaf Blight (*Helminthosporium turcicum* or *Exserohilum turcicum*). A 1 to 9 visual rating indicating the resistance to Northern Leaf Blight. A higher score indicates a higher resistance.

On1: *Ostrinia nubilalis* 1st brood rating (1=resistant to 9=susceptible).

On2: *Ostrinia nubilalis* 2nd brood rating (1=resistant to 9=susceptible).

Percent Identity. Percent identity as used herein refers to the comparison of the homozygous alleles of two inbred lines. Each inbred plant will have the same allele (and therefore be homozygous) at almost all of their loci. Percent identity is determined by comparing a statistically significant number of the homozygous alleles of two inbred lines. For example, a percent identity of 90% between inbred [insert name here] and another inbred line means that the two inbred lines have the same allele at 90% of their loci.

Percent Similarity. Percent similarity as used herein refers to the comparison of the homozygous alleles of an inbred line with another plant. The homozygous alleles of [insert name here] are compared with the alleles of a non-inbred plant, such as a hybrid, and if the allele of the inbred matches at least one of the alleles from the hybrid then they are scored as similar. Percent similarity is determined by comparing a statistically significant number of loci and recording the number of loci with similar alleles as a percentage. For example, a percent similarity of 90% between inbred [insert name here] and a hybrid maize plant means that the inbred line matches at least one of the hybrid alleles at 90% of the loci. In the case of a hybrid produced from [insert name here] as the male or female parent, such hybrid will comprise two sets of alleles, one set of which will comprise the same alleles as the homozygous alleles of inbred line [insert name here].

Plant Height. This is a measure of the height of the plant from the ground to the tip of the tassel in centimeters.

Plant Parts. As used herein, the term "plant parts" includes leaves, stems, roots, seed, grain, embryo, pollen, ovules, flowers, ears, cobs, husks, stalks, root tips, anthers, pericarp, silk, tissue, cells and the like.

Pollen Score. A 1 to 9 visual rating indicating the amount of pollen shed. The higher the score the more pollen shed.

Pollen weight. This is calculated by dry weight of tassels collected as shedding commences minus dry weight from similar tassels harvested after shedding is complete.

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging. Root lodging is the percentage of plants that do not root lodge; plants that lean from the vertical axis at an approximately 30 degree angle or greater would be counted as root lodged.

Root Lodging: Root lodging is the percentage of plants that root lodge. A plant is counted as root lodged if a portion of the plant leans from the vertical axis by approximately 30 degrees or more.

Scatter Grain. A 1 to 9 visual rating indicating the amount of scatter grain (lack of pollination or kernel abortion) on the ear. The higher the score the less scatter grain.

Seedling Color: Color of leaves at the 6 to 8 leaf stage.

Seedling Height: Plant height at the 6 to 8 leaf stage.

Seedling Vigor. This is the visual rating (1 to 9) of the amount of vegetative growth after emergence at the seedling stage (approximately five leaves). A higher score indicates better vigor.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Southern Leaf Blight (*Helminthosporium maydis* or *Bipolaris maydis*). A 1 to 9 visual rating indicating the resistance to Southern Leaf Blight. A higher score indicates a higher resistance.

Southern Rust (*Puccinia polysora*). A 1 to 9 visual rating indicating the resistance to Southern Rust. A higher score indicates a higher resistance.

Sr: *Sphacelotheca reiliana* rating is actual percent infection.

SSR profile: A profile of simple sequence repeats used as genetic markers and scored by gel electrophoresis following PCR amplification using flanking oligonucleotide primers.

Stalk Lodging Score. A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging.

Stalk Lodging: The percentage of plants that did stalk lodge. Plants are counted as stalk lodged if the plant is broken over or off below the ear.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

Stewart's Wilt (*Erwinia stewartii*). A 1 to 9 visual rating indicating the resistance to Stewart's Wilt. A higher score indicates a higher resistance.

SVC: Southeastern Virus Complex (combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel Blast. A 1 to 9 visual rating was used to measure the degree of blasting (necrosis due to heat stress) of the tassel at the time of flowering. A 1 would indicate a very high level of blasting at time of flowering, while a 9 would have no tassel blasting.

Tassel Size. A 1 to 9 visual rating was used to indicate the relative size of the tassel. The higher the rating the larger the tassel.

Tassel Weight. The average weight of a tassel (grams) just prior to pollen shed.

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

The highest maximum temperature used is 86 degrees F. and the lowest minimum temperature used is 50° F.

TR: Stalk rot rating (values represent severity rating of 1=25% of inoculated internode rotted to 9=entire stalk rotted and collapsed).

Unadjusted Test Weight. The measure of the weight of the grain in pounds for a given volume (bushel).

Yield (Bushels/Acre). Yield of the grain at harvest in bushels per acre adjusted to 15% moisture.

Yield: Yield of grain at harvest adjusted to 15.5% moisture.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Origin and Breeding History.

Inbred DS-046358 was derived from the cross between two inbred lines designated parent A and parent B. The origin and breeding history of inbred plant DS-046358 can be summarized as follows: Parent A was crossed to the inbred parent B in nursery rows 640 and 836 in Chile. The S0 seed was grown and self-pollinated in nursery row 0004-11. The S1 seed was grown and self-pollinated in nursery row 5040 in Chile. 11 ears were selected. S2 ears were grown ear-to-row and self pollinated. 3 ears were selected in nursery row 7472 in Clinton, Wis. S3 ears were grown ear-to-row and self pollinated in nursery row 408 in Chile, 3 ears were selected and coded inbred DS-046358. S4 ears were grown ear-to-row and self pollinated in nursery rows 0070-05-0070-07 in Clinton Wis., 3 ears were selected. S5 ears were grown ear-to-row and self pollinated nursery rows 20412-20413 in Clinton, Wis., 4 ears were selected. S6 ears were grown ear-to-row and self pollinated. Final selection was completed in nursery rows 771-774 in Chile. No variant traits are visually evident in DS-046358.

Inbred corn line DS-046358 shows uniformity and stability within the limits of environmental influence for the traits described in Table 1. DS-046358 has been self-pollinated and ear-rowed a sufficient number of generations with careful attention paid to uniformity of plant type to ensure homozygosity and phenotypic stability. No variant traits visually evident in DS-046358.

Inbred corn plants can be reproduced by planting the seeds of a plant of inbred corn line DS-046358, growing the resulting corn plants under self-pollinating or sib-pollinating conditions with adequate isolation using standard techniques well known to an artisan skilled in the agricultural arts. Seeds can be harvested from such a plant using standard, well known procedures.

Phenotypic Description

Inbred maize line DS-046358 is a dent maize inbred that may be used as either a male or female in the production of the first generation F1 maize hybrid, although DS-046358 may be best suited for use as a male. Inbred maize line DS-046358 can be used to produce hybrids ranging in maturity from 101 to 112 crm. Inbred maize line DS-046358 demonstrates good root strength and above average per se yield. In hybrid combination, inbred DS-046358 demonstrates good yield potential, and good root strength.

Inbred maize line DS-046358, being substantially homozygous, can be reproduced by planting seeds of the line, growing the resulting maize plants under self-pollinating or sib-pollinating conditions with adequate isolation, and harvesting the resulting seed using techniques familiar to the agricultural arts.

As used herein, a corn plant having the physiological and morphological characteristics of inbred corn line DS-046358 has the characteristics presented in Table 1.

TABLE 1

Variety Description Information

| Feature | Exhibited by DS-046358 |
|---|---|
| 1. Type | Dent |
| 2. Maturity: Growing Degree Unit | |
| Emergence to 50% of plants in silk | 1443 |
| Emergence to 50% of plants in pollen shed | 1425 |
| 3. Plant: | |
| Plant height (to tassel tip) | 300 cm |
| Tillers | No |
| Average no. of ears per stalk | Single |
| Anthocyanin of brace roots | Moderate |
| 4. Leaf | |

TABLE 1-continued

Variety Description Information

| Feature | Exhibited by DS-046358 |
|---|---|
| Leaf color | Medium green |
| Angle of leaf from stalk | 30-60° |
| Leaf width (widest point of ear node leaf) | 10 cm |
| Leaf margin Color | White |
| 5. Tassel | |
| Silk color (3 days after emergence) | Green |
| Anther color | Green |
| Glume color | Green |
| Number of lateral branches on tassel | 4 |
| 6. Ear | |
| Ear length | 17 cm |
| Number of kernel rows | 16 |
| Alignment of kernel rows | Slightly curved |
| Ear taper | Slight |
| 7. Kernel | |
| Kernel length | 10 mm |
| Pericarp color | Colorless |
| Endosperm type | Normal starch |
| Cob color | Red |
| 8. Other traits | |
| Male Sterile | No |
| Transgenic | No |

The combining ability of a line, as well as the performance of the line per se, is a factor in the selection of improved maize inbreds. Combining ability refers to a line's contribution as a parent when crossed with other lines to form hybrids. The hybrids formed for the purpose of selecting superior lines may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the lines.

General combining ability provides an overall score for the inbred over a large number of test crosses. Specific combining ability provides information on hybrid combinations formed by DS-046358 and a specific inbred parent. A line such as DS-046358 which exhibits good general combining ability may be used in a large number of hybrid combinations. DS-046358 shows good general combining ability for hybrid production.

Deposit Information

At least 2500 seeds from inbred corn seed of the variety designated DS-046358, disclosed above and recited in the appended claims, was deposited with the American Type Culture Collection (ATCC), 10801 University Boulevard, Manassas, Va. 20110 on Mar. 13, 2008 as PTA-9052. The seeds deposited were taken from seeds maintained by Dairyland Seed Co., Inc., West Bend, Wis. 53095 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. Additionally, Applicant has or will satisfy all of the requirements of 37 C.F.R. §§1.801-1.809.

The present invention contemplates using a plant of the corn inbred line DS-046358, or part thereof, or a corn plant having the physiological and morphological characteristics of the DS-046358 corn inbred line, as a source of breeding material for developing a corn plant in a corn breeding program using plant breeding techniques. Plant breeding techniques useful in the developing corn plants include, but are not limited to, single seed descent, modified single seed descent, recurrent selection, reselection, mass selection, bulk selection, backcrossing, pedigree breeding, mutation breeding, restriction fragment length polymorphism enhanced selection, genetic marker enhanced selection, and transformation. Plant breeding techniques are known to the art and have been described in the literature. For example, see U.S. Pat. No. 6,459,022 and U.S. Pat. No. 7,301,082, each of which is incorporated by reference in its entirety.

The present invention further contemplates using a plant of the corn inbred line DS-046358, or part thereof, or a corn plant having the physiological and morphological characteristics of the DS-046358 corn inbred line in plant transformation protocols. Any DNA sequences, whether from a different species or from the same species, which are inserted into the genome using transformation are referred to herein collectively as "transgenes". In some embodiments of the invention, a transformed variant of DS-046358 may contain at least one transgene but could contain at least 1, 2, 3, 4, 5, 6, 7, 8, 9, 10 transgenes and/or no more than 15, 14, 13, 12, 11, 10, 9, 8, 7, 6, 5, 4, 3, or 2 transgenes. Methods for producing transgenic plants are known in the art, and the present invention also relates to transformed versions of the claimed inbred maize line DS-046358 as well as hybrid combinations thereof.

As used herein, the term "plant" includes plant cells, plant protoplasts, plant cell tissue cultures from which corn plants can be regenerated, plant calli, plant clumps, and plant cells that are intact in plants or parts thereof. "Plant part" includes, but is not limited to, embryos, immature embryos, meristematic cells, immature tassels, microspores, leaf, pollen, tassels, anthers, ovules, cotyledon, hypocotyl, root, root tip, flower, silk, kernels, ears, cobs, husks, shoot and stalk, and the like.

One may obtain corn plants according to the present invention by directly by growing the seed of DS-046358, or by any other means. A corn plant having all of the physiological and morphological characteristics of DS-046358 can be obtained by any suitable means, including, but not limited to, regenerating plants or plant parts from tissue culture or cuttings. The scope of the present invention is not limited by the method by which the plant is obtained.

The present invention is not limited to the exemplified embodiments, but is intended to encompass all such modifications and variations as come within the scope of the following claims.

The invention claimed is:

1. A seed of corn inbred line designated DS-046358, representative seed of the line having been deposited under ATCC Accession No. PTA-9052.

2. A plant, or a part thereof, produced by growing the seed of claim 1.

3. Pollen of the plant of claim 2.

4. An ovule of the plant of claim 2.

5. A cell of the plant of claim 2.

6. A plant, or a part thereof, having all the physiological and morphological characteristics of DS-046358, representative seed of the line having been deposited under ATCC Accession No. PTA-9052.

7. A tissue culture of regenerable cells from the plant, or part thereof, of claim 2.

8. The tissue culture of regenerable cells of claim 7, wherein the regenerable cells are derived from a plant part selected from the group consisting of embryos, immature embryos, meristematic cells, immature tassels, microspores, leaf, pollen, tassels, anthers, ovule, cotyledon, hypocotyl, root, root tip, flower, silk, kernels, ears, cobs, husks, shoot and stalk.

9. The tissue culture of claim 7, wherein regenerable cells are protoplasts or callus cells.

10. Protoplasts produced from the tissue culture of claim 7.

11. A plant regenerated from the tissue culture of claim 7, wherein the plant has all of the physiological and morphological characteristics of DS-046358, representative seed of the line having been deposited under ATCC Accession No. PTA-9052.

12. A tissue culture of regenerable cells from the plant, or part thereof, of claim 6.

13. The tissue culture of regenerable cells of claim 12, wherein the regenerable cells are derived from a plant part selected from the group consisting of embryos, immature embryos, meristematic cells, immature tassels, microspores, leaf, pollen, tassels, anthers, ovule, cotyledon, hypocotyl, root, root tip, flower, silk, kernels, ears, cobs, husks, shoot and stalk.

14. The tissue culture of claim 12, wherein regenerable cells are protoplasts or callus cells.

15. Protoplasts produced from the tissue culture of claim 12.

16. A plant regenerated from the tissue culture of claim 12, wherein the plant has all of the physiological and morphological characteristics of DS-046358, representative seed of the line having been deposited under ATCC Accession No. PTA-9052.

17. A method for producing corn seed, comprising crossing a first parent corn plant with a second parent corn plant, at least one of the first and second parent corn plants being of the inbred line designated DS-046358, representative seed of the line having been deposited under ATCC Accession No. PTA-9052 to yield corn seed.

18. The method of claim 17, wherein the first or second corn plant is an inbred corn line distinct from the inbred line designated DS-046358 and the seed is hybrid corn seed.

19. Hybrid corn seed produced by the process of claim 17.

20. A hybrid corn plant produced by growing a seed produced by the process of claim 17.

21. The hybrid corn plant of claim 20, wherein the plant is a first generation ($F_1$) hybrid corn plant.

22. The corn plant of claim 20, further defined as having a genome comprising a single locus conversion, wherein the single locus was stably inserted into the corn genome by transformation.

23. The corn plant of claim 22, wherein the locus is selected from the group consisting of a dominant allele and a recessive allele.

24. The corn plant of claim 22, wherein the locus confers a trait selected from the group consisting of herbicide tolerance; insect resistance; resistance to bacterial, fungal, nematode or viral disease; waxy starch; male sterility and restoration of male fertility.

25. A method of producing an inbred corn plant derived from the inbred corn line designated DS-046358, the method comprising:
(a) preparing a progeny plant derived from the inbred corn line designated DS-046358 by crossing a plant of the inbred corn line designated DS-046358 with a second corn plant, wherein a sample of the seed of the inbred corn line designated DS-046358 was deposited under ATCC Accession No. PTA-9052;
(b) crossing the progeny plant with itself or another corn plant of the inbred corn line designated DS-046358 to produce a seed of a progeny plant of a subsequent generation;
(c) growing a progeny plant of a subsequent generation from said seed and crossing the progeny plant of a subsequent generation with itself or another corn plant of the inbred corn line designated DS-046358; and
(d) repeating steps (b) and (c) for an additional 3-10 generations to produce an inbred corn plant derived from the inbred corn line designated DS-046358.

* * * * *